United States Patent [19]

Coates

[11] Patent Number: 4,616,013

[45] Date of Patent: Oct. 7, 1986

[54] FUSED THIADIAZINES

[75] Inventor: William J. Coates, Welwyn Garden City, England

[73] Assignee: Smith Kline & French Laboratories Limited, Welwyn Garden City, England

[21] Appl. No.: 668,781

[22] Filed: Nov. 6, 1984

[30] Foreign Application Priority Data

Nov. 8, 1983 [GB] United Kingdom ............... 8329784

[51] Int. Cl.$^4$ .................... C07D 285/16; A61K 31/54
[52] U.S. Cl. ........................................ 514/222; 544/9
[58] Field of Search ............................ 544/9; 514/222

[56] References Cited

U.S. PATENT DOCUMENTS

| | | | |
|---|---|---|---|
| 3,464,988 | 9/1969 | Holava et al. | 260/250 |
| 4,423,045 | 12/1983 | Brown et al. | 424/246 |
| 4,489,074 | 12/1984 | Brown et al. | 424/246 |

FOREIGN PATENT DOCUMENTS

A124314 11/1984 European Pat. Off. .

OTHER PUBLICATIONS

Cignarella et al., *Il Farmaco* 37:133 (1982).
Loriga et al., *Il Farmaco* 34:72 (1979).
Cignarella et al., *Il Farmaco* 33:866 (1978).
Curran et al., *J. Med. Chem.*, 17:273 (1974).
Dalton et al., *Aust. J. Chem.* 25:625 (1972).
Holava et al., *J. Med. Chem.* 14:262 (1971).

*Primary Examiner*—John M. Ford
*Attorney, Agent, or Firm*—Edward T. Lentz; Janice E. Williams; Alan D. Lourie

[57] ABSTRACT

This invention relates to thiadiazinone derivatives which have inotropic and vasodilator activity. A specific compound of this invention is 7-acetamido-9,9a-dihydroindeno[1,2-e][1,3,4]thiadiazine-2(3H)-one.

31 Claims, No Drawings

FUSED THIADIAZINES

The present invention relates to heterocyclic compounds and in particular to such compounds having a thiadiazinone ring as part of a tricyclic structure. This invention further relates to processes for their preparation, their use as inotropic agents and to pharmaceutical compositions containing them.

Accordingly the present invention provides compounds of the formula (I):

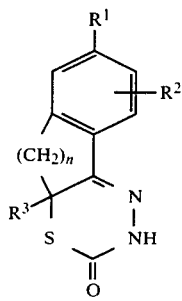

and pharmaceutically acceptable salts thereof, wherein:

$R^1$ is hydrogen, $C_{1-6}$alkyl, halo, cyano, nitro, amino, a group —NHCOR$^4$, a group —COR$^5$, or a group —NHC(NCN)NHR$^6$; wherein $R^4$ is hydrogen, $C_{1-6}$alkoxy, $C_{1-6}$alkyl optionally substituted by phenyl, or $R^4$ is a group NR$^7$R$^8$ wherein $R^7$ and $R^8$ are independently hydrogen, $C_{1-6}$alkyl or benzyl; $R^5$ is hydroxy, hydrogen, $C_{1-6}$alkyl, $C_{1-6}$alkoxy, or a group —NR$^7$R$^8$; and $R^6$ is hydrogen or $C_{1-6}$alkyl;

$R^2$ is hydrogen or $C_{1-4}$alkyl;

$R^3$ is hydrogen or $C_{1-4}$alkyl; and n is one, and when $R^3$ is hydrogen n can also be two.

When used herein alkyl means groups that are either straight-chained or branched. In general preferred alkyl groups are methyl and ethyl. Suitably halo is fluoro, chloro or bromo.

Suitably $R^2$ is $C_{1-4}$alkyl for example methyl. Preferably $R^2$ is hydrogen.

Suitably $R^3$ is hydrogen. Suitably $R^3$ is methyl.

In a favoured aspect n is one thus forming a dihydroindenothiadiazinone ring system. In an alternative aspect n is two thus forming a dihydronaphthothiadiazinone ring system.

In one aspect, in the compounds of the formula (I), $R^1$ is hydrogen, cyano, amino, a group —NHCOR$^4$ or a group —COR$^5$.

Suitably $R^1$ is amino or a group —NHCOR$^4$ as hereinbefore defined such as $C_{1-7}$alkanoylamino for example formamido, acetamido, propionamido or butyramido, $C_{2-7}$alkanoylamino substituted by phenyl for example phenylacetamido, or $C_{1-6}$alkoxycarbonylamino for example methoxycarbonylamino, ethoxycarbonylamino, propoxycarbonylamino or butoxycarbonylamino.

In an alternative aspect $R^1$ is a group —NHCONR$^7$R$^8$ as hereinbefore defined, for example dimethylureido, diethylureido, methylureido, ethylureido or benzylureido.

Suitably $R^1$ is a group COR$^5$ as hereinbefore defined. For example $R^1$ may be a group such as carboxy, $C_{1-7}$alkanoyl for example formyl, acetyl or propionyl, $C_{1-6}$alkoxycarbonyl for example methoxycarbonyl, ethoxycarbonyl, propoxycarbonyl or butoxycarbonyl.

In an alternative aspect $R^1$ may be cyano or a group CONR$^7$R$^8$ wherein $R^7$ and $R^8$ are as hereinbefore defined. For example $R^1$ may be a group such as carbamoyl, $C_{1-6}$alkylcarbamoyl for example methylcarbamoyl or ethylcarbamoyl, di-$C_{1-6}$alkylcarbamoyl for example dimethylcarbamoyl, diethylcarbamoyl or di-propylcarbamoyl, or di-benzylcarbamoyl.

Suitably $R^1$ is a group —NHC(NCN)NHR$^6$ wherein $R^6$ is as hereinbefore defined, for example hydrogen, methyl or ethyl.

In a further aspect $R^1$ may be hydrogen or $C_{1-6}$alkyl for example methyl or ethyl.

More suitably $R^1$ is hydrogen, amino, methyl, fluoro, carbamoyl, $C_{1-6}$alkoxycarbonylamino or $C_{1-7}$alkanoylamino.

Preferably $R^1$ is carbamoyl, methoxycarbonylamino, ethoxycarbonylamino, amino, acetamido, propionamido or butyramido. Of these acetamido and amino are most favoured.

Therefore preferred compounds of this invention are those of the formula (II):

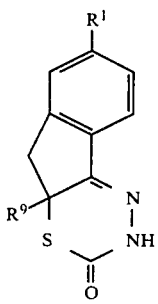

and pharmaceutically acceptable salts thereof wherein $R^9$ is hydrogen or methyl, and $R^1$ is as hereinbefore defined. Suitable and preferred values for $R^1$ in the compounds of the formula (II) are as for $R^1$ in the compounds of the formula (I).

In particular we have found that when $R^1$ is $C_{1-7}$alkanoylamino, $R^9$ is preferably methyl in the compounds of the formula (II).

Specific compounds of this invention include:
9,9a-dihydroindeno[1,2-e][1,3,4]thiadiazin-2(3H)-one,
7-acetamido-9,9a-dihydroindeno[1,2-e][1,3,4]thiadiazin-2(3H)-one,
7-cyano-9,9a-dihydroindeno[1,2-e][1,3,4]thiadiazin-2(3H)-one,
7-carboxamido-9,9a-dihydroindeno[1,2-e][1,3,4]thiadiazin-2(3H)-one,
7-amino-9,9a-dihydroindeno[1,2-e][1,3,4]thiadiazin-2(3H)-one,
7-ethoxycarbonylamino-9,9a-dihydroindeno[1,2-e][1,3,4]-thiadiazin-2(3H)-one,
7-methoxycarbonyl-9,9a-dihydroindeno[1,2-e][1,3,4]-thiadiazin-2(3H)-one,
9,10-dihydro-10aH-naphtho[1,2-e][1,3,4]thiadiazin-2(3H)-one,
7-acetamido-9,10-dihydro-10aH-naphtho[1,2-e][1,3,4]-thiadiazin-2(3H)-one,
9a-methyl-9,9a-dihydroindeno[1,2-e][1,3,4]thiadiazin-2(3H)-one,
7-acetamido-9a-methyl-9,9a-dihydroindeno[1,2-e][1,3,4]-thiadiazin-2(3H)-one,
7-amino-9a-methyl-9,9a-dihydroindeno[1,2-e][1,3,4]-thiadiazin-2(3H)-one,
7-acetamido-9a-ethyl-9,9a-dihydroindeno[1,2-e][1,3,4]-thiadiazin-2(3H)-one, 9a-methyl-7-propionamido-9,9a-dihydroindeno[1,2-e][1,3,4]-thiadiazin-2(3H)-one, 7-ethoxycarbonylamino-9a-methyl-9,9a-dihydroindeno[1,2-e][1,3,4]thiadiazin-2(3H)-one, 9a-methyl-7-($N^2$-methylureido)-9,9a-dihydroindeno[1,2-e][1,3,4]thiadiazin-2(3H)-one, 7-($N^2$-cyano-$N^3$-methylguanidino)-9a-methyl-9,9a-dihydroindeno[1,2-e][1,3,4]thiadiazin-2(3H)-one, 7-cyano-9a-methyl-9,9a-dihydroindeno[1,2-e][1,3,4]-thiadiazin-2(3H)-one, 7-carboxamido-9a-methyl-9,9a-dihydroindeno[1,2-e][1,3,4]-thiadiazin-2(3H)-one, 7-carboxy-9a-methyl-9,9a-dihydroindeno[1,2-e][1,3,4]-thiadiazin-2(3H)-one, 7-dimethylcarboxamido-9a-methyl-9,9a-dihydroindeno[1,2-e][1,3,4]thiadiazin-2(3H)-one, 7-methylcarboxamido-9a-methyl-9,9a-dihydroindeno[1,2-e][1,3,4]thiadiazin-2(3H)-one, 7-fluoro-9a-methyl-9,9a-dihydroindeno[1,2-e][1,3,4]-thiadiazin-2(3H)-one, and 7,9a-dimethyl-9,9a-dihydroindeno1,2-e][1,3,4]thiadiazin-2(3H)-one, and pharmaceutically acceptable salts thereof.

This invention covers all tautomeric forms of the compounds of the formulae (I) and (II) and all optical isomeric forms thereof.

Compounds of the formulae (I) and (II) having a free amino group may form pharmaceutically acceptable acid-addition salts with either organic or inorganic acids, for example those formed with hydrochloric, hydrobromic, hydriodic, methanesulphonic, sulphuric, maleic, fumaric, succinic, acetic, oxalic, tartaric, citric and lactic acids. Any carboxy group present may be optionally salified, for example with a metal ion, such as an alkali metal for example sodium and potassium, or an alkaline earth metal for example calcium and magnesium. The ability to form acid-addition and/or metal salts will be subject to the nature of the relevant compounds as will be readily understood by one skilled in the art.

In order to use a compound of the formula (I) or a pharmaceutically acceptable salt thereof for the treatment of mammals including humans it is normally formulated in accordance with standard pharmaceutical practice as a pharmaceutical composition.

Compounds of the formula (I) and their pharmaceutically acceptable salts may be administered orally, parenterally, trans-dermally or rectally.

Compounds of the formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include magnesium stearate, starch, lactose and sucrose.

Typical parenteral compositions consist of a solution or suspension of the compound or salt in a sterile aqueous carrier or parenterally acceptable oil.

A typical suppository formulation comprises a compound of the formula (I) or a pharmaceutically acceptable salt thereof which is active when administered in this way, with a binding and/or lubricating agent for example gelatin or cocoa-butter or other low melting vegetable waxes or fats.

Preferably the composition is in unit dosage form for example a tablet or capsule so that the patient may administer to himself a single dose.

Each dosage unit contains preferably from 5 to 250 mg of a compound of the formula (I) or a pharmaceutically acceptable salt thereof calculated as the free base.

The daily dosage regimen for an adult human patient is from about 5 mg to about 1500 mg of the compound of the formula (I) or a pharmaceutically acceptable salt thereof calculated as the free base. The active ingredient may be administered from 1 to 6 times a day, sufficient to increase cardiac output. The compositions of the present invention have positive inotropic activity and vasodilator activity and are of use in the treatment of cardiovascular diseases which can be treated by compounds having either or both of these activities. One such disease condition is congestive heart failure.

The compounds of this invention may be co-administered with other pharmaceutically active compounds. Conveniently the compounds of this invention and the other active compound or compounds are formulated in a pharmaceutical composition. Examples of compounds which may be included in pharmaceutical compositions with the compounds of the formula (I) are vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, cardioglycosides for example digoxin and digitoxin, calcium antagonists for example verapamil and nifedipine, diuretics such as thiazides and related compounds for example benzdrofluazide, chloro-thiazide, chlorothalidone, hydrochlorothiazide, and other diuretics for example frusemide and triamterene, and sedatives for example nitrazepam, flurazepam and diazepam.

In another aspect the present invention provides a process for the preparation of a compound of the formula (I) or a pharmaceutically acceptable salt thereof, which process comprises:

(a) for preparing a compound of the formula (I) wherein $R^3$ is hydrogen, dealkylating a compound of the formula (III):

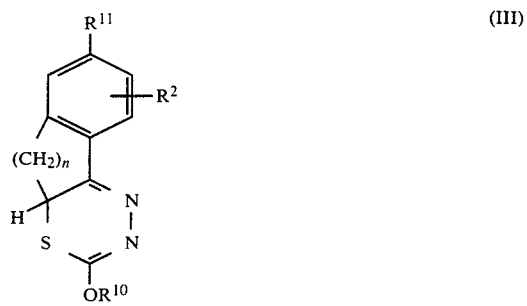

(III)

wherein n and $R^2$ are as hereinbefore defined, $R^{11}$ is a group $R^1$ as hereinbefore defined or a precursor thereof, and $R^{10}$ is $C_{1-4}$alkyl; or (b) cyclizing a compound of the formula (IV):

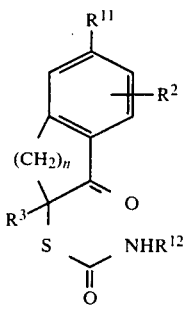

wherein $R^2$, $R^3$, n and $R^{11}$ are as hereinbefore defined, and $R^{12}$ is optionally protected amino, in the presence of acid;
and thereafter if necessary:
(i) converting a group $R^{11}$ to a group $R^1$,
(ii) removing any protecting group,
(iii) forming a pharmaceutically acceptable salt.

Suitably the dealkylation of a compound of the formula (III) is performed in an organic solvent for example a $C_{1-4}$alkanol such as ethanol, or acetonitrile, generally at an elevated temperature for example under reflux conditions. Generally the compound of the formula (III) is not isolated, but is prepared and reacted in situ.

Suitably $R^{10}$ is methyl.

Suitably the cyclization of a compound of the formula (IV) is performed in an aqueous inorganic acid, for example hydrochloric acid, or in an organic solvent containing an aqueous inorganic acid, for example in a $C_{1-6}$alkanol, such as ethanol in admixture with hydrochloric acid. The cyclization is conveniently performed at an elevated temperature for example 60° C. to 140° C., preferably at reflux temperature for convenience.

The cyclization may be performed on a compound of the formula (IV) wherein $R^{12}$ is amino, or a protected variant of the compound of the formula (IV), for example protected on the hydrazine function by an acid-labile protecting group for example isopropylidene or benzylidene i.e. $R^{12}$ is $-N=C(CH_3)_2$ or $-N=CHC_6H_5$.

An example of $R^{11}$ being a precursor of a group $R^1$ is when $R^{11}$ is an isocyanate (—NCO) group which may react with an amine of formula $NHR^7R^8$, for example in an organic aprotic solvent such as dimethylformamide, at an ambient temperature. Compounds wherein $R^{11}$ is —NCO may be prepared via reaction of a corresponding amino compound with a carbonylating agent, for example N,N-carbonyldiimidazole, and need not be isolated. Such agents may be reacted in conventional manner, for example in an aprotic solvent such as dimethylformamide, at an ambient temperature or with cooling, for example at about 0° C. The reaction is performed in the presence of an organic base, for example triethylamine.

Compounds of the formula (I) wherein $R^1$ is a nitro group can be reduced to a corresponding amino compound in conventional manner, for example via catalytic hydrogenation, either using hydrogen gas or via catalytic transfer hydrogenation. Suitable catalysts include transition metal catalysts suitable for use in the presence of a sulphur-containing compound.

Compounds of the formula (I) wherein $R^1$ is amino may be converted to compounds of the formula (I) wherein $R^1$ is a group —NHCOR$^4$ by conventional methods of acylation, for example using an acid halide, an acid anhydride or an activated ester.

Compounds of the formula (I) wherein $R^1$ is a group —NHCONHR$^7$ may be formed by reacting a compound of the formula (I) wherein $R^1$ is amino with an appropriate isocyanate. The reaction is conveniently performed in an inert solvent such as dimethylformamide at an ambient or elevated temperature for example at room temperature or at a temperature up to about 100° C.

Compounds of the formula (I) wherein $R^1$ is a group —NHC(NCN)NHR$^6$ may be formed by reacting a compound of the formula (I) wherein $R^1$ is amino with a compound of the formula: L—C(NCN)NHR$^6$ wherein L is a leaving group such as $C_{1-6}$alkylthio or benzylthio, in a solvent such as pyridine at a non-extreme temperature. In an alternative such compounds can be prepared by reacting a compound of the formula (I) wherein $R^1$ is amino with a compound of the formula: $L^1$—C(NCN)—$L^2$ wherein $L^1$ and $L^2$ are leaving groups such as $C_{1-6}$alkoxy, phenoxy, benzyloxy or $C_{1-6}$alkylthio, conveniently in the presence of an organic base for example triethylamine; and thereafter reacting with a $C_{1-6}$alkylamine ($R^6NH_2$).

In the dealkylation of the compound of the formula (III) or in the cyclization of the compound of the formula (IV), $R^{11}$ may be a protected amino group that is convertible to amino by conventional methods of deprotection, for example by chemical or enzymic hydrolysis or by hydrogenolysis, for example $R^{11}$ may be an appropriate group $R^1$ as hereinbefore defined or a benzyloxycarbonylamino group.

Compounds of the formula (I) wherein $R^1$ is carboxy may be prepared by the hydrolysis of a corresponding compound wherein $R^1$ (or $R^{11}$) is an esterified carboxy (—CO$_2$R) group. Compounds of the formula (I) wherein $R^1$ is carbamoyl may be prepared by the hydrolysis of a corresponding compound wherein $R^1$ is cyano.

Compounds of the formula (I) wherein $R^5$ is $C_{1-6}$alkoxy or a group —NR$^7R^8$ may be prepared by reacting a compound of the formula (I) wherein $R^5$ is hydroxy or an activated derivative thereof with a $C_{1-6}$alkanol or an amine of the formula NHR$^7R^8$.

Pharmaceutically acceptable salts of the compounds of the formula (I) may be prepared in conventional manner, for example acid addition salts may be prepared by treating those compounds containing a basic group of the formula (I) with the appropriate acid in a $C_{1-4}$alkanol, or they may be prepared by the use of an ion-exchange resin to form the desired salt directly from the free base or via a different acid addition salt.

The compounds of the formula (III) may be conveniently prepared by reacting of a compound of the formula (V):

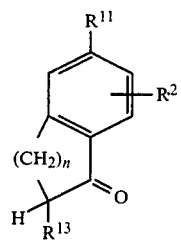

wherein $R^2$, $R^{11}$ and n are as hereinbefore defined, and $R^{13}$ is halo, with a compound of the formula (VI):

R¹⁰OCSNHNH₂ (VI)

wherein R¹⁰ is C₁₋₄alkyl. Suitably R¹³ is bromo or chloro, preferably bromo. Suitably R¹⁰ is methyl. Conveniently the reaction of the compounds of the formulae (V) and (VI) is performed in an organic solvent for example a C₁₋₄alkanol such as ethanol, or in acetonitrile. The reaction is conveniently performed at an elevated temperature for example under reflux conditions. The compound of the formula (III) is generally converted in situ under these conditions to form a corresponding thiadiazinone compound.

The compounds of the formula (V) may be conveniently prepared by halogenating a compound of the formula (VII):

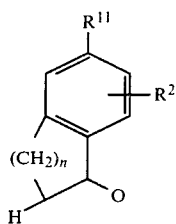

(VII)

wherein R², R¹¹ and n are as hereinbefore defined. Suitably to prepare compounds wherein R¹³ is bromo, the reaction is performed in a chlorinated organic solvent, for example chloroform with a solution of bromine. The reaction is conveniently performed at a non-extreme temperature such as between −20° and 60° C., preferably between 0° and 30° C.

The compounds of the formula (IV) may be conveniently prepared by reacting a compound of the formula (VIII):

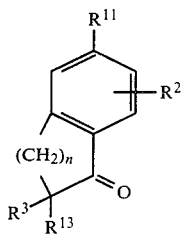

(VIII)

wherein R², R³, R¹¹, R¹³ and n are as hereinbefore defined, with a compound of the formula (IX):

M⊕⊖O—CS—NHR¹² (IX)

wherein R¹² is as hereinbefore defined and M⁺ is a counter-ion, for example an alkali metal ion such as potassium or sodium or is an ammonium ion.

Suitably the reaction of the compounds of the formulae (VIII) and (IX) is performed in an organic solvent such as a C₁₋₄alkanol, dimethylformamide or acetonitrile. The reaction is conveniently performed at a non-extreme temperature for example between −10° C. and 80° C., preferably between 0° and 30° C.

The compound of the formula (IV) need not be isolated but may be cyclized in situ in the presence of acid as hereinbefore described.

If it is desired to prepare a protected compound of the formula (IV) then the compound of the formula (IX) may be in protected form, for example as the isopropylidene. In an alternative the compound of the formula (IV) may be protected, if desired, after the reaction of the compounds of the formulae (VIII) and (IX).

The compounds of the formula (VIII) are preparable in analogous manner to the compounds of the formula (V).

The following Descriptions and Examples serve to illustrate this invention.

DESCRIPTION 1

5-Nitro-2-bromoindan-1-one

Bromine (1.79 ml) in chloroform (125 ml) was added dropwise over 15 minutes to a stirred solution of 5-nitroindan-1-one (6.17 g) in chloroform (200 ml) at 5° C. The stirred solution was allowed to warm to room temperature and after one hour, when the bromine colour had discharged, the solution was washed with water and dried. Evaporation of the filtered solution under reduced pressure afforded an oil which was diluted with methanol and crystallised (with seeding) to give 5-nitro-2-bromoindan-1-one, m.p. 88.5°–90.5° C. (recrystallised from methanol).

DESCRIPTIONS 2-11

In a similar manner to Description 1, the appropriate indanone or tetralone afforded the following 2-bromo derivatives: 5-acetamido-2-bromoindan-1-one, m.p. 176°–7° C. dec (from acetonitrile); 2-bromo-5-cyanoindan-1-one, m.p. 127°–8° C. (from methanol); 2-bromo-5-ethoxycarbonylaminoindan-1-one, m.p. 198°–9° C. (from aqueous dimethylformamide); 2-bromo-5-methoxycarbonylindan-1-one, m.p. 105°–6° C. (from acetonitrile); 5-acetamido-2-bromo-2-methylindan-1-one, m.p. 154°–156° C. (from ethanol); 2-bromo-5-ethoxycarbonylamino-2-methylindan-1-one, m.p. 149°–151° C. (after column chromatography); 2-bromo-5-cyano-2-methylindan-1-one, m.p. 95°–6° C. (from methanol); 2-bromo-2,5-dimethylindan-1-one, m.p. 59°–63° C. (after trituration with ether); 5-acetamido-2-bromo-2-ethylindan-1-one, m.p. 141°–143° C. (from benzene/60–80 petroleum ether); 6-acetamido-2-bromo-1-tetralone, m.p. 162°–4° C. (after column chromatography).

DESCRIPTION 12

2-Bromo-5-carboxy-2-methylindan-1-one

Bromine (0.57 ml) was added dropwise during 15 minutes to a stirred solution of 5-carboxy-2-methylindan-1-one (2 g) in acetic acid (75 ml) at 35° C. The solution was stirred for a further 30 minutes then evaporated to low volume under reduced pressure and the residue was diluted with water to give 2-bromo-5-carboxy-2-methylindan-1-one, m.p. 203°–205° C. (from acetic acid).

DESCRIPTION 13

5-Acetamido-2-methylindan-1-one and
5-amino-2-methylindan-1-one (i) A solution of 2-methyl-3-(3-nitrophenyl)propionic acid (105 g) in aqueous sodium hydroxide (20.4 g in 700 ml) was hydrogenated at 50 psi over 10% palladium on carbon (4.0 g). After removal of the catalyst, the solution was cooled and concentrated hydrochloric acid (85 ml) was added, followed at 10° by the addition of acetic anhydride (53 ml) and sodium acetate trihydrate (76.0 g). The mixture was stirred for one hour to give 3-(3- acetamidophenyl)-2-methylpropionic acid (107.2 g; mp 138.5–140.5).

(ii) A stirred mixture of 3-(3-acetamidophenyl)-2-methylpropionic acid (50.0 g) and aluminium trichloride (181 g) was treated on an oil bath (170°) for 25 minutes. The warm melt was poured with stirring on to ice (1.5 kg) and the resulting mixture extracted with dichloromethane (1 L). The residue from evaporation of the organic extract was heated under reflux with 2N hydrochloric acid (400 ml) for 15 minutes. The cooled solution was washed with dichloromethane (2×100 ml, 2×50 ml) and neutralised with 40% sodium hydroxide to give 24.45 g of solid product. A further 1.38 g was obtained by extraction of the filtrate and back-extraction of the dichloromethane washings. Recrystallisation from methanol or acetonitrile gave pure 5-amino-2-methyl-1-indanone (m.p. 151°–152.5°).

This was dissolved in acetic acid, acetylated with acetic anhydride, evaporated and triturated under water (containing a little methanol) to give the acetamido compound, m.p. 136°–138° C.

DESCRIPTION 14

5-Acetamido-2-ethylindan-1-one and 5-amino-2-ethylindan-1-one

In a manner similar to Description 13, 2-ethyl-3-(3-nitrophenyl)propenoic acid was reduced and acetylated to give 2-(3-acetamidobenzyl)butanoic acid, m.p. 131°–132° C. (from aqueous ethanol) which was cyclised and the product hydrolysed to afford 5-amino-2-ethylindan-1-one, m.p. 105.5°–108° C. (from acetonitrile). Acetylation of the latter afforded 5-acetamido-2-ethylindan-1-one, m.p. 154°–155° C. (from acetonitrile).

DESCRIPTION 15

5-Cyano-2-methylindan-1-one

A solution of 5-amino-2-methyl-1-indanone (10.0 g) in fluoroboric acid (40%; 28.0 ml) was treated at 0°–5° C. with sodium nitrite (4.7 g) in water (8.0 ml). The diazonium salt solution was added to cuprous cyanide (25.0 g) and potassium cyanide (37.5 g) in water (100 ml) at 40°. The mixture was stirred at 10° for 10 minutes, cooled and extracted with chloroform. The extract was evaporated and the residue recrystallised from aqueous ethanol to give 5-cyano-2-methyl-1-indanone(7.89 g; m.p. 90°–91° C.).

DESCRIPTION 16

5-Carboxy-2-methylindan-1-one

A stirred mixture of 5-cyano-2-methylindan-1-one (9.36 g), glacial acetic acid (90 ml) and concentrated hydrochloric acid (90 ml) was heated under reflux for 20 hours to afford 5-carboxy-2-methylindan-1-one, m.p. 189°–194° C. (from aqueous ethanol).

DESCRIPTION 17

5-Ethoxycarbonylaminoindan-1-one

5-Aminoindan-1-one was dissolved in the minimum of hot pyridine and the solution was cooled to 0° C. Ethyl chloroformate (1.2 mole equivalents) was added dropwise to the cold stirred solution which was then stirred for one hour at room temperature. Evaporation under reduced pressure and trituration of the residue with water afforded 5-ethoxycarbonylaminoindan-1-one, m.p. 181°–2° C. (from ethanol).

DESCRIPTION 18

5-Ethoxycarbonylamino-2-methylindan-1-one

In a similar manner to Description 17, 5-amino-2-methylindan-1-one afforded 5-ethoxycarbonylamino-2-methylindan-1-one, m.p. 159°–161° C. (from ethanol).

EXAMPLE 1

9,9a-Dihydroindeno[1,2-e][1,3,4]thiadiazin-2(3H)-one

A stirred mixture of methoxythiocarbonylhydrazine (7.5 g) and 2-bromoindan-1-one (10.0 g) in acetonitrile (100 ml) was heated under reflux for 3 hours, allowed to cool and filtered. The filtered solution was evaporated under reduced pressure to low volume to afford the title compound as a solid which was recrystallised from acetonitrile to give 9,9a-dihydroindeno[1,2-e][1,3,4]-thiadiazin-2(3H)-one, m.p. 171°–173° C.

EXAMPLE 2

7-Nitro-9,9a-dihydroindeno[1,2-e][1,3,4]thiadiazin-2(3H)-one

In a manner similar to that of Example 1, 5-nitro-2-bromoindan-1-one and methoxythiocarbonylhydrazine afforded 7-nitro-9,9a-dihydroindeno[1,2-e][1,3,4]thiadiazin-2(3H)-one, m.p. 252°–254° C. (dec) (from dimethylformamide-acetone).

EXAMPLE 3

7-Acetamido-9,9a-dihydroindeno[1,2-e][1,3,4]thiadiazin-2(3H)-one (a) In a manner similar to that of Example 1, 5-acetamido-2-bromoindan-1-one and methoxythiocarbonylhydrazine afforded 7-acetamido-9,9a-dihydroindeno[1,2-e][1,3,4]thiadiazin-2(3H)-one, m.p. 261°–262° C. (dec) (from aqueous ethanol).

(b) In a manner similar to that of Example 12, reaction of 2-bromo-5-acetamidoindan-1-one with potassium thiocarbazate followed by acid treatment afforded the title compound, m.p. 275°–278° C. (dec) (from aqueous dimethylformamide).

EXAMPLE 4

7-Cyano-9,9a-dihydroindeno[1,2-e][1,3,4]thiadiazin-2(3H)-one

In a manner similar to that of Example 1, 5-cyano-2-bromoindan-1-one and methoxythiocarbonylhydrazine afforded 7-cyano-9,9a-dihydroindeno[1,2-e][1,3,4]-thiadiazin-2(3H)-one, m.p. 269°–272° C. (from acetonitrile).

EXAMPLE 5

7-Carboxamido-9,9a-dihydroindeno[1,2-e][1,3,4]thiadiazin-2(3H)-one

7-Cyano-9,9a-dihydroindeno[1,2-e][1,3,4]thiadiazin-2(3H)-one (2.45 g) in concentrated sulphuric acid (20 ml) was heated with stirring to 90° C. for 20 minutes. The mixture was cooled, poured on to crushed ice (150 g), neutralised with 50% sodium hydroxide solution and the solid product was collected by filtration. This was recrystallised from dimethylformamide-water to afford 7-carboxamido-9,9a-dihydroindeno[1,2-e][1,3,4]thiadiazin-2(3H)-one, m.p. >300° C.; δ(DMSO-$d_6$) 3.0 and 3.67 (2H, 2m), 4.66 (1H, dd), 7.4 (3H, broad), 7.6–8.0 (3H, m).

EXAMPLE 6

7-Amino-9,9a-dihydroindeno[1,2-e][1,3,4]thiadiazin-2(3H)-one

7-Acetamido-9,9a-dihydroindeno[1,2-e][1,3,4]thiadiazin-2(3H)-one (2.84 g) in 6N hydrochloric acid (25 ml) was heated with stirring to reflux for 30 minutes. The mixture was cooled to room temperature, neutralised with solid potassium carbonate and the solid product was collected by filtration. This was recrystallised from dimethylformamide-water to afford 7-amino-9,9a-dihydroindeno[1,2-e][1,3,4]thiadiazin-2(3H)-one, slow decomposition >250° C.; δ(DMSO-$d_6$) 2.8 and 3.45 (2H, 2m), 4.4 (1H, dd), 5.73 (2H, br s), 6.6 (2H, m), 7.36 (1H, d).

EXAMPLE 7

7-Ethoxycarbonylamino-9,9a-dihydroindeno[1,2-e][1,3,4]-thiadiazin-2(3H)-one

In a manner similar to that of Example 12, reaction of 2-bromo-5-ethoxycarbonylaminoindan-1-one with potassium thiocarbazate followed by acid treatment afforded the title compound, m.p. 225°–226° C. (from aqueous ethanol).

EXAMPLE 8

7-Methoxycarbonyl-9,9a-dihydroindeno[1,2-e][1,3,4]-thiadiazin-2(3H)-one

In a manner similar to that of Example 12, reaction of 2-bromo-5-methoxycarbonylindan-1-one with potassium thiocarbazate followed by acid treatment afforded the title compound, m.p. 225°–226° C. (from acetonitrile).

EXAMPLE 9

9,10-Dihydro-10aH-naphtho[1,2-e][1,3,4]thiadiazin-2(3H)-one

In a manner similar to that of Example 1, methoxythiocarbonylhydrazine and 2-bromo-1-tetralone afforded 9,10-dihydro-10aH-naphtho[1,2-e][1,3,4]thiadiazin-2(3H)-one which on recrystallisation from acetonitrile had m.p. 148°–50° C. and 155°–6° C. (two forms) which re-melted at 155°–6° C.

EXAMPLE 10

7-Acetamido-9,10-dihydro-10aH-naphtho[1,2-e][1,3,4]-thiadiazin-2(3H)-one

In a manner similar to that of Example 1, reaction of 2-bromo-6-acetamino-1-tetralone with methoxythiocarbonylhydrazine afforded the title compound, m.p. 256°–257° C. (after column chromatography and recrystallisation from aqueous dimethylformamide).

EXAMPLE 11

9a-Methyl-9,9a-dihydroindeno[1,2-e][1,3,4]thiadiazin-2(3H)-one

2-Bromo-2-methylindan-1-one (5.7 g) was added in portions, over a few minutes, to a stirred mixture of potassium thiocarbazate (3.62 g) and dimethylformamide (28.5 ml) at 5° C. The temperature was allowed to rise slowly to room temperature and after 3½ hours the mixture was evaporated under reduced pressure. The residue was treated with water (150 ml) and extracted into diethyl ether. The diethyl ether extracts were combined, dried and evaporated under reduced pressure to a low volume to afford S-(2-methyl-1-oxo-2-indanyl)-thiocarbazate m.p. 153°–5° C. (recrystallised from ethyl acetate).

A stirred suspension of S-(2-methyl-1-oxo-2-indanyl)-thiocarbazate (2.4 g) in 2N hydrochloric acid (60 ml) containing a small amount of n-butanol was heated under reflux for 5 minutes. The mixture was cooled and filtered to afford 9a-methyl-9,9a-dihydroindeno[1,2-e]-[1,3,4]thiadiazin-2(3H)-one, m.p. 192°–4° C. (recrystallised from acetonitrile).

EXAMPLE 12

7-Acetamido-9a-methyl-9,9a-dihydroindeno[1,2-e]-1,3,4-thiadiazin-2(3H)-one

In a manner similar to that of Example 11, potassium thiocarbazate (1.02 g) was reacted with 5-acetamido-2-bromo-2-methylindan-1-one (2.0 g). After evaporation of dimethylformamide the residue was triturated with water (40 ml) and filtered. The filtrate of S-(5-acetamido-2-methyl-1-oxo-2-indanyl)thiocarbazate was acidified (pH 1–2) with concentrated hydrochloric acid and heated on a steam bath for 5 minutes. The mixture was cooled and filtered to afford 7-acetamido-9a-methyl-9,9a-dihydroindeno[1,2-e][1,3,4]thiadiazin-2(3H)-one, m.p. 259°–261° C. (dec.) (from aqueous acetic acid).

EXAMPLE 13

7-Amino-9a-methyl-9,9a-dihydroindeno[1,2-e][1,3,4]-thiadiazin-2(3H)-one

A stirred mixture of 7-acetamido-9a-methyl-9,9a-dihydroindeno[1,2-e][1,3,4]thiadiazin-2(3H)-one (6 g), 6N hydrochloric acid (60 ml) and 1-butanol (1 ml) was heated under reflux for 25 minutes. The solution was cooled in ice and neutralised with concentrated aqueous sodium hydroxide solution to afford the title compound, m.p. 232.5°–234° C. (from acetonitrile).

EXAMPLE 14

7-Acetamido-9a-ethyl-9,9a-dihydroindeno[1,2-e][1,3,4]-thiadiazin-2(3H)-one

In a manner similar to that of Example 12, reaction of 5-acetamido-2-bromo-2-ethylindan-1-one with potassium thiocarbazate followed by acid treatment afforded the title compound, m.p. 204°–207° C. (after column chromatography and recrystallisation from acetonitrile).

EXAMPLE 15

9a-Methyl-7-propionamido-9,9a-dihydroindeno[1,2-e][1,3,4]-thiadiazin-2(3H)-one

A mixture of 7-amino-9a-methyl-9,9a-dihydroindeno-[1,2-e][1,3,4]thiadiazin-2(3H)-one (1.55 g), propionic acid (10 ml) and propionic anhydride (1.28 ml) was heated on a steam bath for 20 minutes. After evaporation the residue was triturated with water containing methanol to afford the title compound, m.p. 258°–259.5° C. (dec) (from aqueous ethanol).

EXAMPLE 16

7-Ethoxycarbonylamino-9a-methyl-9,9a-dihydroindeno[1,2-e]-[1,3,4]thiadiazin-2(3H)-one In a manner similar to that of Example 12, reaction of 2-bromo-5-ethoxycarbonylamino-2-methylindan-1-one with potassium thiocarbazate followed by acid treatment gave the title compound, m.p. 230°–231° C. (after column chromatography and recrystallisation from ethanol).

EXAMPLE 17

9a-Methyl-7-(N²-methylureido)-9,9a-dihydroindeno[1,2-e]-[1,3,4]thiadiazin-2(3H)-one Methyl isocyanate (0.66 ml) was added dropwise to a boiling solution of 7-amino-9a-methyl-9,9a-dihydroindeno-[1,2-e][1,3,4]thiadiazin-2(3H)-one (1.17 g) in dry ethanol (45 ml). The stirred mixture was heated under reflux for a further 45 minutes, then cooled and filtered to afford the title compound, m.p. 239°–240° C. (from aqueous ethanol).

EXAMPLE 18

7-(N²-Cyano-N³-methylguanidino)-9a-methyl-9,9a-dihydroindeno[1,2-e][1,3,4]thiadiazin-2(3H)-one A stirred mixture of 7-amino-9a-methyl-9,9a-dihydroindeno[1,2-e][1,3,4]thiadiazin-2(3H)-one (1.03 g), N-cyanodiphenyliminocarbonate (1.5 g) and acetonitrile (200 ml) was heated under reflux for 24 hours. The mixture was cooled to afford 7-(N²-cyano-O-phenylisoureido)-9a-methyl-9,9a-dihydroindeno[1,2-e][1,3,4]-thiadiazin-2(3H)-one, m.p. 233°–235° C.

A stirred solution of the above intermediate (0.5 g) in 33% methylamine in ethanol (20 ml) was heated under reflux for 45 minutes. After evaporation of the solvent the residue was triturated with water to afford the title compound, m.p. >300° C. (from aqueous dimethylformamide); $\nu$(Nujol mull); 2164 cm$^{-1}$ (vs, sharp, CN); $\delta$(DMSO-d$_6$, 100 MHz) 1.50 (s, C$\overline{\text{CH}}_3$); 2.83 (d, NH$\overline{\text{CH}}_3$); 3.22 (s, CH$_2$); 7.32 (m, N$\overline{\text{H}}$CH$_3$ and 6,8-H); 7.51 (d, 5-H); 9.0 (br, s, guanidine N¹-H); 11.49 (br, s, thiadiazinone NH).

EXAMPLE 19

7-Cyano-9a-methyl-9,9a-dihydroindeno[1,2-e][1,3,4]-thiadiazin-2(3H)-one

In a manner similar to that of Example 12, reaction of 2-bromo-5-cyano-2-methylindan-1-one with potassium thiocarbazate followed by acid treatment afforded the title compound, m.p. 248°–250° C. (dec) (from acetonitrile).

EXAMPLE 20

7-Carboxamido-9a-methyl-9,9a-dihydroindeno[1,2-e][1,3,4]-thiadiazin-2(3H)-one

In a manner similar to that of Example 5, hydrolysis of 7-cyano-9a-methyl-9,9a-dihydroindeno[1,2-e][1,3,4]-thiadiazin-2(3H)-one with concentrated sulphuric acid afforded the title compound which was recrystallised from dimethylformamide; >250° C. (slow decomposition); $\delta$(DMSO-d$_6$, 100 MHz) 1.51 (s, CH$_3$); 3.32 (s, CH$_2$); 7.60 (br, d, CONH$_2$); 7.72 (d, 5-H); ca 7.90 (m, 6,8-H): 11.70 (br s, NH).

EXAMPLE 21

7-Carboxy-9a-methyl-9,9a-dihydroindeno[1,2-e][1,3,4]-thiadiazin-2(3H)-one

In a manner similar to that of Example 12, reaction of 2-bromo-7-carboxy-2-methylindan-1-one with potassium thiocarbazate followed by acid treatment afforded the title compound, m.p. 296°–298° C. (dec) (from aqueous ethanol).

EXAMPLE 22

7-Dimethylcarboxamido-9a-methyl-9,9a-dihydroindeno[1,2-e]-[1,3,4]thiadiazin-2(3H)-one A mixture of 7-carboxy-9a-methyl-9,9a-dihydroindeno-[1,2-e][1,3,4]thiadiazin-2(3H)-one (0.86 g) and thionyl chloride (9 ml) was heated under reflux for 30 minutes. Excess of thionyl chloride was removed by distillation after the addition of toluene. Dimethylamine gas was passed into the resultant solution of the acid chloride in toluene (10 ml) at room temperature until the reaction subsided. The mixture was stirred for a further 30 minutes then heated on a steam bath for 10 minutes. The residue left after evaporation was triturated with water to give the title compound m.p. 258°–260° C. (dec) (from aqueous ethanol).

EXAMPLE 23

7-Methylcarboxamido-9a-methyl-9,9a-dihydroindeno[1,2-e]-[1,3,4]thiadiazin-2(3H)-one In a manner similar to that of Example 22, treatment of the intermediate acid chloride with methylamine afforded the title oompound, m.p. 227°–230° C. (from aqueous ethanol).

EXAMPLE 24

7-Fluoro-9a-methyl-9,9a-dihydroindeno[1,2-e][1,3,4]-thiadiazin-2(3H)-one

In a manner similar to that of Example 11, reaction of 2-bromo-5-fluoro-2-methylindan-1-one with potassium thiocarbazate gave S-(5-fluoro-2-methyl-1-oxo-2-indanyl)thiocarbazate, m.p. 147.5°–148.5° C. (from 2-propanol) which was treated with acid as before to afford the title compound, m.p. 200°–202° C. (from ethanol).

EXAMPLE 25

7,9a-Dimethyl-9,9a-dihydroindeno[1,2-e][1,3,4]thiadiazin-2(3H)-one

In a manner similar to that of Example 11, reaction of 2-bromo-2,5-dimethylindan-1-one with potassium thiocarbazate gave S-(2,5-dimethyl-1-oxo-2-indanyl)thiocarbazate which was treated with acid as before to afford the title compound, m.p. 164°–165° C. (from 2-propanol).

EXAMPLE 26

| Ingredients | Amounts |
|---|---|
| 7-acetamido-9,9a-dihydroindeno[1,2-e]-[1,3,4]thiadiazin-2(3H)-one | 100 mg |
| Sucrose | 40 mg |
| Starch | 15 mg |
| Talc | 3 mg |
| Stearic acid | 1 mg |

The ingredients are screened, mixed and filled into a hard gelatin capsule. Such capsules are administered orally from 1 to 4 times daily to a patient in need of improved cardiac function.

The other compounds of this invention can be formulated in a similar manner.

Test Method

The activity of the compounds for use in this invention as cardiac stimulants, also known as cardiotonic agents, is demonstrated by a positive inotropic effect.

The compounds of formula (I) and their pharmaceutically acceptable salts are tested for cardiac stimulant activity following a procedure based on that of S. C. Verma and J. H. McNeill (J. Pharm & Exp. Therapeutics, 200, 352-362 (1977)). Guinea pigs (500-700 g) of either sex are sacrificed and the hearts are quickly removed and transferred to a dissecting dish containing oxygenated bathing fluid. While in the bathing medium, the right ventricle is cut into two strips. The strips are each suspended in a 75 ml bath containing Krebs Henseleit solution at 37° C., and the bath is bubbled with 95% oxygen and 5% carbon dioxide. The ventricular strips are electrically stimulated at a frequency of 0.5 Hz, at double the threshold voltage. A resting tension of 1.0 g is applied to the strips and the tension is kept constant by readjustment during an equilibration period of 60 minutes. The bathing fluid is frequently changed during this period. When a steady base line is obtained, a compound under test is added to the bathing fluid and a cumulative concentration response curve is plotted. The compounds for use in the present invention which were tested resulted in a 50% increase in the force of contraction of the ventricular strips at concentrations ($EC_{50}$ value) in the bathing fluid of less than $10^{-4}$ molar, thus showing that they have activity as positive inotropic agents. All of the Examples of the invention show good activity in the above test system. In particular the compounds of Examples 3, 5, 10, 12, 15, 17, 20 and 24 show $EC_{50}$ values below $5 \times 10^{-6}$ molar; and the compounds of Examples 6, 9, 11, 16, 18, 19, 21 and 25 give $EC_{50}$ values in the range $5-50 \times 10^{-6}$. Amrinone (5-amino-3,4'-bipyrid-6(1H)-one), a known compound of interest in this therapeutic category gives an $EC_{50}$ value of $15 \times 10^{-6}$ molar. The compounds of this invention show no overt signs of toxicity at doses up to approximately 10 times a predicted therapeutic dose. The compounds of Examples 3 and 12 have been shown when administered intravenously in 20% polyethylene glycol to conscious dogs, to increase left ventricular dp/dt max by at least 50% at dosage levels of 0.1 mg/Kg and below. There were no statistically significant changes in blood pressure or heart rate.

What is claimed is:

1. A compound of the formula (I):

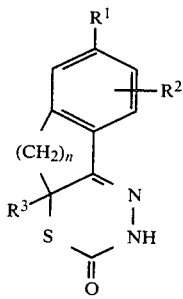

or a pharmaceutically acceptable salt thereof, wherein:
$R^1$ is hydrogen, $C_{1-6}$alkyl, halo, cyano, nitro, amino, a group —$NHCOR^4$, a group —$COR^5$, or a group —$NHC(NCN)NHR^6$; wherein $R^4$ is hydrogen, $C_{1-6}$alkoxy, $C_{1-6}$alkyl optionally substituted by phenyl, or $R^4$ is a group $NR^7R^8$ wherein $R^7$ and $R^8$ are independently hydrogen, $C_{1-6}$alkyl or benzyl; $R^5$ is hydroxy, hydrogen, $C_{1-6}$alkyl, $C_{1-6}$alkoxy, or a group —$NR^7R^8$; and $R^6$ is hydrogen or $C_{1-6}$alkyl;
$R^2$ is hydrogen or $C_{1-4}$alkyl;

$R^3$ is hydrogen or $C_{1-4}$alkyl; and
n is one, and when $R^3$ is hydrogen n can also be two.

2. A compound according to claim 1 wherein $R^1$ is hydrogen, cyano, amino, a group —$NHCOR^4$ or a group —$COR^5$.

3. A compound according to either claim 1 or claim 2 wherein n is one.

4. A compound according to claim 1 wherein $R^2$ is hydrogen and $R^3$ is hydrogen or methyl.

5. A compound according to claim 1 wherein $R^1$ is hydrogen, amino, carbamoyl, $C_{1-6}$alkoxycarbonylamino or $C_{1-7}$alkanoylamino.

6. A compound according to claim 5 wherein $R^1$ is amino or acetamido.

7. A compound according to claim 1 which is a compound selected from the group consisting of:
9,9a-dihydroindeno[1,2-e][1,3,4]thiadiazin-2(3H)-one,
7-acetamido-9,9a-dihydroindeno[1,2-e][1,3,4]thiadiazin-2(3H)-one,
7-cyano-9,9a-dihydroindeno[1,2-e][1,3,4]thiadiazin-2(3H)-one,
7-carboxamido-9,9a-dihydroindeno[1,2-e][1,3,4]thiadiazin-2(3H)-one,
7-amino-9,9a-dihydroindeno[1,2-e][1,3,4]thiadiazin-2(3H)-one,
7-ethoxycarbonylamino-9,9a-dihydroindeno[1,2-e][1,3,4]-thiadiazin-2(3H)-one,
7-methoxycarbonyl-9,9a-dihydroindeno[1,2-e][1,3,4]-thiadiazin-2(3H)-one,
9,10-dihydro-10aH-naphtho[1,2-e][1,3,4]thiadiazin-2(3H)-one,
7-acetamido-9,10-dihydro-10aH-naphtho[1,2-e][1,3,4]-thiadiazin-2(3H)-one,
9a-methyl-9,9a-dihydroindeno[1,2-e][1,3,4]thiadiazin-2(3H)-one,
7-acetamido-9a-methyl-9,9a-dihydroindeno[1,2-e]-[1,3,4]-thiadiazin-2(3H)-one,
7-amino-9a-methyl-9,9a-dihydroindeno[1,2-e][1,3,4]-thiadiazin-2(3H)-one,
7-acetamido-9a-ethyl-9,9a-dihydroindeno[1,2-e][1,3,4]-thiadiazin-2(3H)-one,
9a-methyl-7-propionamido-9,9a-dihydroindeno[1,2-e][1,3,4]-thiadiazin-2(3H)-one,
7-ethoxycarbonylamino-9a-methyl-9,9a-dihydroindeno[1,2-e][1,3,4]thiadiazin-2(3H)-one,
9a-methyl-7-($N^2$-methylureido)-9,9a-dihydroindeno[1,2-e][1,3,4]thiadiazin-2(3H)-one,
7-($N^2$-cyano-$N^3$-methylguanidino)-9a-methyl-9,9a-dihydroindeno[1,2-e][1,3,4]thiadiazin-2(3H)-one,
7-cyano-9a-methyl-9,9a-dihydroindeno[1,2-e][1,3,4]-thiadiazin-2(3H)-one,
7-carboxamido-9a-methyl-9,9a-dihydroindeno[1,2-e]-[1,3,4]-thiadiazin-2(3H)-one,
7-carboxy-9a-methyl-9,9a-dihydroindeno[1,2-e][1,3,4]-thiadiazin-2(3H)-one,
7-dimethylcarboxamido-9a-methyl-9,9a-dihydroindeno[1,2-e][1,3,4]thiadiazin-2(3H)-one,
7-methylcarboxamido-9a-methyl-9,9a-dihydroindeno[1,2-e][1,3,4]thiadiazin-2(3H)-one,
7-fluoro-9a-methyl-9,9a-dihydroindeno[1,2-e][1,3,4]-thiadiazin-2(3H)-one, or
7,9a-dimethyl-9,9a-dihydroindeno[1,2-e][1,3,4]thiadiazin-2(3H)-one,
or a pharmaceutically acceptable salt thereof.

8. A compound according to claim 1 which is 7-acetamido-9a-methyl-9,9a-dihydroindeno[1,2-e][1,3,4]thiadiazin-2(3H)-one.

9. A compound according to claim 1 which is 7-ethoxycarbonylamino-9,9a-dihydroindeno[1,2,e][1,3,4]-thiadiazin-2(3H)-one.

10. A compound according to claim 1 which is 7-acetamido-9,9a-dihydroindeno[1,2,e][1,3,4]-thiadiazin-2(3H)-one.

11. A compound according to claim 1 which is 7-carboxamido-9a-methyl-9,9a-dihydroindeno[1,2,e][1,3,4]-thiadiazin-2(3H)-one.

12. A method for treating cardiac disease in a mammal comprising administering an effective dose of a compound of claim 1.

13. A method for stimulating cardiac activity in a mammal comprising administering an effective doese of a compound of claim 1.

14. A pharmaceutical composition for stimulating cardiac activity in a mammal which comprises an effective amount to produce said effect of a compound according to claim 1 and a pharmaceutically acceptable carrier.

15. A pharmaceutical composition for stimulating cardiac activity in a mammal which comprises an effective amount to produce said effect of a compound according to claim 7 and a pharmaceutically acceptable carrier.

16. A pharmaceutical composition for stimulating cardiac activity in a mammal which comprises an effective amount to produce said effect of a compound according to claim 8 and a pharmaceutically acceptable carrier.

17. A pharmaceutical composition for stimulating cardiac activity in a mammal which comprises an effective amount to produce said effect of a compound according to claim 9 and a pharmaceutically acceptable carrier.

18. A pharmaceutical composition for stimulating cardiac activity in a mammal which comprises an effective amount to produce said effect of a compound according to claim 10 and a pharmaceutically acceptable carrier.

19. A pharmaceutical composition for stimulating cardiac activity in a mammal which comprises an effective amount to produce said effect of a compound according to claim 11 and a pharmaceutically acceptable carrier.

20. A method for producing a positive inotropic effect in a mammal comprising administering an effective dose of a compound of claim 1.

21. A method for producing a positive inotropic effect in a mammal comprising administering an effective dose of a compound of claim 7.

22. A method for producing a positive inotropic effect in a mammal comprising administering an effective dose of a compound of claim 8.

23. A method for producing a positive inotropic effect in a mammal comprising administering an effective does of a compound of claim 9.

24. A method for producing a positive inotropic effect in a mammal comprising administering an effective dose of a compound of claim 10.

25. A method for producing a positive inotropic effect in a mammal comprising administering an effective dose of a compound of claim 11.

26. A method for stimulating cardiac activity in a mammal comprising administering an effective dose of a compound of claim 7.

27. A method for stimulating cardiac activity in a mammal comprising administering an effective dose of a compound of claim 8.

28. A method for stimulating cardiac activity in a mammal comprising administering an effective dose of a compound of claim 9.

29. A method for stimulating cardiac activity in a mammal comprising administering an effective dose of a compound of claim 10.

30. A method for stimulating cardiac activity in a mammal comprising administering an effective dose of a compound of claim 11.

31. A process for the preparation of a compound of the formula (I):

or a or a pharmaceutically acceptable salt thereof, wherein:

$R^1$ is hydrogen, $C_{1-6}$alkyl, halo, cyano, nitro, amino, a group —NHCOR$^4$, a group —COR$^5$, or a group —NH(NCN)NHR$^6$; wherein $R^4$ is hydrogen, $C_{1-6}$alkoxy, $C_{1-6}$alkyl optionally substituted by phenyl, or $R^4$ is a group NR$^7$R$^8$ wherein $R^7$ and $R^8$ are independently hydrogen, $C_{1-6}$alkyl or benzyl; $R^5$ is hydroxy, hydrogen $C_{1-6}$alkyl, $C_{1-6}$alkoxy, or a group —NR$^7$R$^8$; and $R^6$ is hydrogen or $C_{1-6}$alkyl;

$R^2$ is hydrogen or $C_{1-4}$ alkyl;

$R^3$ is hydrogen; and n is 1 or 2, which comprises heating a compound of the formula (III):

wherein n and $R^2$ are as hereinbefore defined, $R^{11}$ is a group $R^1$ as hereinbefore defined or a precursor thereof, and $R^{10}$ is $C_{1-4}$alkyl in an organic solvent thereby dealkylating the group —OR$^{10}$.

* * * * *